United States Patent
Boualleg et al.

(10) Patent No.: US 12,280,361 B2
(45) Date of Patent: Apr. 22, 2025

(54) SELECTIVE HYDROGENATION CATALYST OBTAINED FROM MOLTEN SALTS AND AN ORGANIC ADDITIVE

(71) Applicant: IFP Energies nouvelles, Rueil-Malmaison (FR)

(72) Inventors: Malika Boualleg, Rueil-Malmaison (FR); Laetitia Jothie, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 315 days.

(21) Appl. No.: 17/784,205

(22) PCT Filed: Dec. 4, 2020

(86) PCT No.: PCT/EP2020/084662
§ 371 (c)(1),
(2) Date: Jun. 10, 2022

(87) PCT Pub. No.: WO2021/122061
PCT Pub. Date: Jun. 24, 2021

(65) Prior Publication Data
US 2023/0047217 A1  Feb. 16, 2023

(30) Foreign Application Priority Data
Dec. 17, 2019 (FR) ..................... 1914601

(51) Int. Cl.
*B01J 23/755* (2006.01)
*B01J 21/04* (2006.01)
*B01J 35/30* (2024.01)
*B01J 37/02* (2006.01)
*B01J 37/08* (2006.01)
*C07C 5/05* (2006.01)

(52) U.S. Cl.
CPC ............ *B01J 23/755* (2013.01); *B01J 21/04* (2013.01); *B01J 35/393* (2024.01); *B01J 35/394* (2024.01); *B01J 37/0217* (2013.01); *B01J 37/0228* (2013.01); *B01J 37/0236* (2013.01); *B01J 37/088* (2013.01); *C07C 5/05* (2013.01); *C07C 2521/04* (2013.01); *C07C 2523/755* (2013.01)

(58) Field of Classification Search
CPC ........ B01J 23/755; B01J 21/04; B01J 35/393; B01J 35/394; B01J 37/0217; B01J 37/0228; B01J 37/0236; B01J 37/088; B01J 35/613; B01J 35/635; B01J 35/647; B01J 37/0081; B01J 37/18; B01J 37/0203; B01J 37/0207; C07C 5/05; C07C 2521/04; C07C 2523/755; Y02E 60/50; C10G 49/04
See application file for complete search history.

(56) References Cited

U.S. PATENT DOCUMENTS

| | | | |
|---|---|---|---|
| 5,036,032 A | 7/1991 | Iglesia et al. | |
| 9,486,789 B2 | 11/2016 | Decottignies et al. | |
| 2008/0076660 A1* | 3/2008 | Reyes | B01J 37/0203 502/64 |
| 2017/0001863 A1* | 1/2017 | Park | B01J 35/397 |
| 2020/0338531 A1 | 10/2020 | Boualleg et al. | |

FOREIGN PATENT DOCUMENTS

| | | |
|---|---|---|
| EP | 2921227 B1 | 4/2017 |
| FR | 3076747 A1 | 7/2019 |
| GB | 191308864 A | 4/1914 |

OTHER PUBLICATIONS

Liu et al. ("Ind. Eng. Chem. Res. 2014, 53, 5792-5800") (Year: 2014).*
International Search Report PCT/EP2020/084662 dated Dec. 18, 2020 (pp. 1-3).

* cited by examiner

*Primary Examiner* — Ali Z Fadhel
(74) *Attorney, Agent, or Firm* — Millen, White, Zelano & Branigan, P.C.; Csaba Henter

(57) ABSTRACT

A selective hydrogenation catalyst that can be obtained by the process comprising at least the following steps:
a) the alumina support is brought into contact with at least one organic additive;
b) the alumina support is brought into contact with at least one nickel metal salt, the melting point of said metal salt of which is between 20° C. and 150° C.;
c) the solid mixture obtained on conclusion of steps a) and b) is heated with stirring;
d) the catalyst precursor on conclusion of step c) is dried;
e) a step of heat treatment of the dried catalyst precursor obtained on conclusion of step d) is carried out.

15 Claims, No Drawings

SELECTIVE HYDROGENATION CATALYST OBTAINED FROM MOLTEN SALTS AND AN ORGANIC ADDITIVE

TECHNICAL FIELD

The present invention relates to a catalyst intended particularly for the hydrogenation of unsaturated hydrocarbons and more particularly the selective hydrogenation of polyunsaturated compounds.

PRIOR ART

Many synthesis processes are known from the prior art for improving the reducibility of the metal phase or else for controlling the particle sizes. Among these methods, the use of molten salts as precursors of the active phase of a catalyst or of a trapping mass is known from the literature.

For example, document U.S. Pat. No. 5,036,032 discloses a method for the preparation of a cobalt-based supported catalyst by bringing a support in contact (of the order of a few tens of seconds) in a bath of molten cobalt nitrate salt, followed by a step of drying and of reduction without intermediate calcination. This method makes possible the preferential localization of the cobalt phase at the periphery of the support. However, the method does not allow a precise control of the amount of active phase (here cobalt) deposited due to the very short contact time and furthermore the type of catalyst obtained is not suitable for use in a reactor operating in the liquid phase with a catalyst in suspension (referred to as a "slurry reactor" or "slurry") owing to the excessive loss of metal by attrition. Moreover, the absence of a calcination step is risky since the reaction between the reduction element and the nitrates in the solid is highly exothermic. Finally, this method makes it necessary to handle large amounts of (toxic) cobalt nitrate in liquid form and at temperature, with ratios of approximately 4 grams of active-phase precursors per 1 gram of support. The catalysts obtained by this preparation route are used for the Fischer-Tropsch synthesis of hydrocarbons.

It is known, from Chem. Mater., 1999, 11, pp. 1999-2007, to prepare mixed phosphates via a route of molten salts type. The reaction mixture contains a metal precursor salt (in particular $Ni(NO_3)_2$ or $Co(NO_3)_2$), a source of phosphorus ($NH_4HPO_4$) and an alkali metal (Na or K) nitrate. These preparations are carried out at high temperatures of the order of 400° C. to 450° C. Solids of mixed phosphates type are obtained, for example $Na_3Ni_2(P_2O_7)PO_4$, $K_2Ni_4(PO_4)_2P_2O_7$ or $Na_9CO_3(PO_4)_5$. These solids can find applications in ion exchange, in high-temperature ion conduction or in catalysis.

Document GB 191308864 discloses a process for the synthesis of a bulk catalyst based on nickel or on cobalt for the production of hydrogen by steam reforming. These catalysts can be obtained by liquefaction of metal salts at moderate temperatures, then poured into a mold before calcination heat treatment.

The publication by J.-Y. Tilquin entitled "*Intercalation of CoCl₂ into Graphite: Mixing Method vs Molten Salt Method*", published in Carbon, 35(2), pp. 299-306, 1997, proposes the use, in molten salt form, of a $CoCl_2$—NaCl mixture at high temperature (450-580° C.) for intercalation between graphite sheets. These graphite intercalation compounds find applications in catalysis for the reduction of oxygen in polymer electrolyte fuel cells.

Document EP 2921227 discloses a Fischer-Tropsch catalyst based on a group VIIIB metal deposited on an oxide support comprising alumina, silica, a spinel and phosphorus and also the process for manufacturing same. This process comprises the preparation of the oxide support and also the impregnation of this support with an aqueous solution of a metal precursor followed by drying and calcining. In case of high contents of metals, the impregnation/drying/calcining of the active phase in several steps is preferred.

Subject of the Invention

The present invention thus relates to a new type of selective hydrogenation catalyst comprising performance levels that are at least as good as, or even better than, the catalysts according to the prior art, while at the same time using an amount of nickel-based active phase that is at least equal to, or even lower than, that typically used in the prior art. The process for preparing the catalyst according to the invention leads to a catalyst having a nickel particle size of less than 18 nm, conferring a high intrinsic activity of the nickel active phase. Furthermore, the process for preparing the catalyst used in the context of the present invention makes it possible, without addition of solvent and therefore in a very limited number of steps and above all fewer than the conventional preparation (i.e. by impregnation), to obtain a catalyst of which the catalytic performance levels are at least as good as or even superior to conventional catalysts.

The present invention relates to a selective hydrogenation catalyst comprising a nickel-based active phase and an alumina support, said active phase not comprising a metal from Group VIB, said catalyst comprising a content of elemental nickel of greater than or equal to 1% by weight and less than 20% by weight relative to the total weight of the catalyst, the size of the nickel particles in the catalyst, measured in oxide form, is less than 18 nm, said catalyst being capable of being obtained by the process comprising at least the following steps:

a) the alumina support is brought into contact with at least one organic additive comprising oxygen and/or nitrogen, the molar ratio of the organic additive to the nickel being greater than 0.05 mol/mol;

b) the alumina support is brought into contact with at least one nickel metal salt, at a temperature of less than the melting point of said nickel metal salt, in order to form a solid mixture, the ratio by weight of said metal salt to the alumina support being between 0.1 and 2.3, steps a) and b) being carried out either successively in this order, or simultaneously;

c) the solid mixture obtained on conclusion of steps a) and b) is heated with stirring to a temperature between the melting point of said metal salt and 200° C., in order to obtain a catalyst precursor;

d) the catalyst precursor on conclusion of step c) is dried at a temperature of less than 250° C. in order to obtain a dried catalyst precursor;

e) a step of heat treatment of the dried catalyst precursor obtained on conclusion of step d) is carried out at a temperature of between 250 and 1000° C.

Preferably, the size of the nickel particles in the catalyst, measured in oxide form, is between 0.5 and 12 nm, more preferentially between 1 and 5 nm.

Another subject according to the invention relates to a process for preparing a selective hydrogenation catalyst comprising a nickel-based active phase and an alumina support, said active phase not comprising a metal from Group VIB, said catalyst comprising a content of elemental nickel of greater than or equal to 1% by weight and less than 20% by weight relative to the total weight of the catalyst, the nickel particle size in the catalyst, measured in oxide form, being less than 18 nm, said process comprising the following steps:
- a) the alumina support is brought into contact with at least one organic additive comprising oxygen and/or nitrogen, the molar ratio of the organic additive to the nickel being greater than 0.05 mol/mol;
- b) the alumina support is brought into contact with at least one nickel metal salt, at a temperature of less than the melting point of said nickel metal salt, in order to form a solid mixture, the ratio by weight of said metal salt and the alumina support being between 0.1 and 2.3, steps a) and b) being carried out successively in this order, or simultaneously;
- c) the solid mixture obtained on conclusion of steps a) and b) is heated with stirring to a temperature between the melting point of said metal salt and 200° C., in order to obtain a catalyst precursor;
- d) the catalyst precursor on conclusion of step c) is dried at a temperature of less than 250° C. in order to obtain a dried catalyst precursor;
- e) a step of heat treatment of the dried catalyst precursor obtained on conclusion of step d) is carried out at a temperature of between 250 and 1000° C.

Preferably, the melting point of said metal salt is between 20° C. and 150° C.

Preferably, the molar ratio of said organic additive introduced in step a) to the element nickel introduced in step b) is between 0.1 and 5.0 mol/mol.

In one embodiment according to the invention, steps a) and b) are carried out simultaneously.

Preferably, the organic additive is chosen from aldehydes including from 1 to 14 carbon atoms per molecule, ketones or polyketones including from 3 to 18 carbon atoms per molecule, ethers and esters including from 2 to 14 carbon atoms per molecule, alcohols or polyalcohols including from 1 to 14 carbon atoms per molecule and carboxylic acids or polycarboxylic acids including from 1 to 14 carbon atoms per molecule, or a combination of the various functional groups above.

More preferentially, said organic additive of step a) is chosen from formic acid, formaldehyde, acetic acid, citric acid, oxalic acid, glycolic acid, malonic acid, levulinic acid, ethanol, methanol, ethyl formate, methyl formate, paraldehyde, acetaldehyde, γ-valerolactone acid, glucose and sorbitol.

More preferentially, the organic additive is chosen from citric acid, formic acid, glycolic acid, levulinic acid and oxalic acid.

Preferably, step c) is carried out by means of a pan operating at a speed of between 4 and 70 revolutions per minute.

Preferably, in step b), the ratio by weight of said metal salt to the alumina support is between 0.2 and 2.

Another subject according to the invention relates to a process for the selective hydrogenation of polyunsaturated compounds containing at least 2 carbon atoms per molecule, contained in a hydrocarbon feedstock having a final boiling point below or equal to 300° C., which process being carried out at a temperature of between 0° C. and 300° C., at a pressure of between 0.1 and 10 MPa, at a hydrogen/(polyunsaturated compounds to be hydrogenated) mole ratio of between 0.1 and 10 and at an hourly space velocity of between 0.1 and 200 $h^{-1}$ when the process is carried out in the liquid phase, or at a hydrogen/(polyunsaturated compounds to be hydrogenated) mole ratio of between 0.5 and 1000 and at an hourly space velocity of between 100 and 40 000 $h^{-1}$ when the process is carried out in the gas phase, in the presence of a catalyst according to the invention or obtained according to the preparation process according to the invention.

DETAILED DESCRIPTION OF THE INVENTION

Definitions

Subsequently, the groups of chemical elements are given according to the CAS classification (CRC Handbook of Chemistry and Physics, published by CRC Press, editor-in-chief D. R. Lide, 81st edition, 2000-2001). For example, group VIII according to the CAS classification corresponds to the metals of columns 8, 9 and 10 according to the new IUPAC classification.

The specific surface of the catalyst or of the support used for the preparation of the catalyst according to the invention is understood to mean the BET specific surface determined by nitrogen adsorption in accordance with the standard ASTM D 3663-78 drawn up from the Brunauer-Emmett-Teller method described in the journal "The Journal of the American Chemical Society", 60, 309 (1938).

In the present application, the term "to comprise" is synonymous with (means the same thing as) "to include" and "to contain", and is inclusive or open and does not exclude other elements not stated. It is understood that the term "comprise" includes the exclusive and closed term "consist".

The term "macropores" is understood to mean pores, the opening of which is greater than 50 nm.

The term "mesopores" is understood to mean pores, the opening of which is between 2 nm and 50 nm, limits inclusive.

The term "micropores" is understood to mean pores, the opening of which is less than 2 nm.

Total pore volume of the catalyst or of the support used for the preparation of the catalyst according to the invention is understood to mean the volume measured by mercury intrusion porosimetry according to the standard ASTM D4284-83 at a maximum pressure of 4000 bar (400 MPa), using a surface tension of 484 dyne/cm and a contact angle of 140°. The wetting angle was taken equal to 140° following the recommendations of the publication "Techniques de l'ingénieur, traité analyse et caractérisation" [Techniques of the Engineer, Analysis and Characterization Treatise], pages 1050-1055, written by Jean Charpin and Bernard Rasneur.

In order to obtain better accuracy, the value of the total pore volume corresponds to the value of the total pore volume measured by mercury intrusion porosimetry measured on the sample minus the value of the total pore volume measured by mercury intrusion porosimetry measured on the same sample for a pressure corresponding to 30 psi (approximately 0.2 MPa).

The volume of the macropores and of the mesopores is measured by mercury intrusion porosimetry according to the standard ASTM D4284-83 at a maximum pressure of 4000 bar (400 MPa), using a surface tension of 484 dyne/cm and a contact angle of 140°. The value from which the mercury fills all the intergranular voids is set at 0.2 MPa and it is considered that, above this, the mercury penetrates into the pores of the sample.

The macropore volume of the catalyst or of the support used for the preparation of the catalyst according to the invention is defined as being the cumulative volume of mercury introduced at a pressure of between 0.2 MPa and 30 MPa, corresponding to the volume present in the pores with an apparent diameter of greater than 50 nm.

The mesopore volume of the catalyst or of the support used for the preparation of the catalyst according to the invention is defined as being the cumulative volume of mercury introduced at a pressure of between 30 MPa and 400 MPa, corresponding to the volume present in the pores with an apparent diameter of between 2 and 50 nm.

The volume of the micropores is measured by nitrogen porosimetry. The quantitative analysis of the microporosity is carried out starting from the "t" method (method of Lippens-De Boer, 1965), which corresponds to a transform of the starting adsorption isotherm, as described in the work "Adsorption by Powders and Porous Solids. Principles, Methodology and Applications", written by F. Rouquérol, J. Rouquérol and K. Sing, Academic Press, 1999.

The median mesopore diameter is also defined as being the diameter such that all the pores, among the combined pores constituting the mesopore volume, with a size of less than this diameter constitute 50% of the total mesopore volume determined by mercury porosimetry intrusion.

The median macropore diameter is also defined as being the diameter such that all the pores, among the combined pores constituting the macropore volume, with a size of less than this diameter constitute 50% of the total macropore volume determined by mercury porosimetry intrusion.

The term "size of the nickel particles" is understood to mean the diameter of the nickel crystallites in oxide form. The diameter of the nickel crystallites in oxide form is determined by X-ray diffraction, from the width of the diffraction line located at the angle $2\theta=43°$ (that is to say, along the crystallographic direction [200]) using the Scherrer relationship. This method, used in X-ray diffraction on polycrystalline samples or powders, which links the full width at half maximum of the diffraction peaks to the size of the particles, is described in detail in the reference: Appl. Cryst. (1978), 11, 102-113, "Scherrer after sixty years: A survey and some new results in the determination of crystallite size", J. I. Langford and A. J. C. Wilson.

The nickel content is measured by X-ray fluorescence.
Catalyst

The nickel content in said catalyst according to the invention is greater than or equal to 1% by weight and less than 20% by weight of elemental nickel relative to the total weight of the catalyst, more preferentially between 2% and 19% by weight and even more preferentially between 3% and 19% by weight and even more preferentially 5% and 18% by weight relative to the total weight of the catalyst.

The active phase of the catalyst does not comprise a metal from Group VIB. In particular, it does not comprise molybdenum or tungsten. Preferably, the catalyst comprises an active phase consisting solely of nickel and of an alumina support.

The size of the nickel particles in the catalyst, measured in oxide form, is less than 18 nm, preferably less than 15 nm, more preferentially between 0.5 and 12 nm, in a preferred way between 1 and 8 nm, in an even more preferred way between 1 and 6 nm and more preferentially still between 1 and 5 nm.

Said catalyst is generally presented in all the forms known to those skilled in the art, for example in the form of beads (generally having a diameter of between 1 and 8 mm), of extrudates, of blocks or of hollow cylinders. Preferably, it consists of extrudates with a diameter generally of between 0.5 and 10 mm, preferably between 0.8 and 3.2 mm and very preferably between 1.0 and 2.5 mm and with a mean length of between 0.5 and 20 mm. The term "mean diameter" of the extrudates is understood to mean the mean diameter of the circle circumscribed in the cross section of these extrudates. The catalyst can advantageously be presented in the form of cylindrical, multilobal, trilobal or quadrilobal extrudates. Preferably, its form will be trilobal or quadrilobal. The shape of the lobes will be able to be adjusted according to all the known methods of the prior art.

The specific surface of the catalyst is generally greater than or equal to 30 $m^2/g$, preferably greater than or equal to 50 $m^2/g$, more preferentially between 60 $m^2/g$ and 500 $m^2/g$ and more preferentially still between 70 $m^2/g$ and 400 $m^2/g$.

The total pore volume of the catalyst is generally between 0.1 and 1.5 $cm^3/g$, preferably between 0.35 and 1.2 $cm^3/g$, and more preferentially still between 0.4 and 1.0 $cm^3/g$, and more preferentially still between 0.45 and 0.9 $cm^3/g$.

The catalyst advantageously exhibits a macropore volume of less than or equal to 0.6 ml/g, preferably of less than or equal to 0.5 ml/g, more preferentially of less than or equal to 0.4 ml/g and more preferentially still of less than or equal to 0.3 ml/g.

The mesopore volume of the catalyst is generally at least 0.10 ml/g, preferably at least 0.20 ml/g, in a preferred way between 0.25 ml/g and 0.80 ml/g and in a more preferred way between 0.30 and 0.65 ml/g.

The median mesopore diameter of the catalyst is advantageously between 3 and 25 nm, preferably between 6 and 20 nm and particularly preferably between 8 and 18 nm.

The catalyst advantageously exhibits a median macropore diameter of between 50 and 1,500 nm, preferably between 80 and 1,000 nm and more preferably still of between 250 and 800 nm.

Preferably, the catalyst exhibits a low microporosity; very preferably, it does not exhibit any microporosity.
Support According to the invention, the support is an alumina, that is to say that the support comprises at least 95%, preferably at least 98% and particularly preferably at least 99% by weight of alumina, relative to the weight of the support. The alumina generally exhibits a crystallographic structure of the δ-, γ- or θ-alumina type, alone or as a mixture.

According to the invention, the alumina support can comprise impurities such as oxides of metals from Groups IIA, IIIB, IVB, IIB, IIIA and IVA according to the CAS classification, preferably silica, titanium dioxide, zirconium dioxide, zinc oxide, magnesium oxide and calcium oxide, or also alkali metals, preferably lithium, sodium or potassium, and/or alkaline earth metals, preferably magnesium, calcium, strontium or barium, or also sulfur.

The specific surface of the support is generally greater than or equal to 30 $m^2/g$, preferably greater than or equal to 50 $m^2/g$, more preferentially between 60 $m^2/g$ and 500 $m^2/g$ and more preferentially still between 70 $m^2/g$ and 400 $m^2/g$.

The total pore volume of the support is generally between 0.1 and 1.5 $cm^3/g$, preferably between 0.35 and 1.2 $cm^3/g$, and more preferentially still between 0.4 and 1.0 $cm^3/g$, and more preferentially still between 0.45 and 0.9 $cm^3/g$.

The support advantageously exhibits a macropore volume of less than or equal to 0.6 ml/g, preferably of less than or equal to 0.5 ml/g, more preferentially of less than or equal to 0.4 ml/g and more preferentially still of less than or equal to 0.3 ml/g.

The mesopore volume of the support is generally at least 0.10 ml/g, preferably at least 0.20 ml/g, in a preferred way between 0.25 ml/g and 0.80 ml/g and in a more preferred way between 0.30 and 0.65 ml/g.

The median mesopore diameter of the support is advantageously between 3 and 25 nm, preferably between 6 and 20 nm and particularly preferably between 8 and 18 nm.

The support advantageously exhibits a median macropore diameter of between 50 and 1500 nm, preferably between 80 and 1000 nm and more preferably still of between 250 and 800 nm.

Preferably, the support exhibits a low microporosity; very preferably, it does not exhibit any microporosity.

Preparation Process

The steps of the process for the preparation of the catalyst are described in detail below.

Step a)

According to step a) of the process for the preparation of the catalyst, the support is brought into contact with at least at least one organic additive comprising oxygen and/or nitrogen, preferably chosen from aldehydes including from 1 to 14 carbon atoms per molecule (preferably from 2 to 12), ketones or polyketones including from 3 to 18 (preferably from 3 to 12) carbon atoms per molecule, ethers or esters including from 2 to 14 (preferably from 3 to 12) carbon atoms per molecule, alcohols or polyalcohols including from 1 to 14 (preferably from 2 to 12) carbon atoms per molecule and carboxylic acids or polycarboxylic acids including from 1 to 14 (preferably from 1 to 12) carbon atoms per molecule. The organic additive can be composed of a combination of the various functional groups mentioned above.

Preferably, the organic additive is chosen from formic acid HCOOH, formaldehyde $CH_2O$, acetic acid $CH_3COOH$, citric acid, oxalic acid, glycolic acid (HOOC—$CH_2$—OH), malonic acid (HOOC—$CH_2$—COOH), levulinic acid ($CH_3CCH_2CH_2CO_2H$), ethanol, methanol, ethyl formate $HCOOC_2H_5$, methyl formate $HCOOCH_3$, paraldehyde ($CH_3$—CHO)$_3$, acetaldehyde $C_2H_4O$, γ-valerolactone acid ($C_5H_8O_2$), glucose and sorbitol.

Particularly preferably, the organic additive is chosen from citric acid, formic acid, glycolic acid, levulinic acid and oxalic acid.

In one embodiment according to the invention, said step a) is carried out by bringing the support into contact with at least one organic additive in the form of a powder.

In another embodiment according to the invention, said step a) is carried out by bringing the support into contact with at least one organic additive in the form of a powder dissolved in a minimum amount of water. Minimum amount of water is understood to mean the amount of water making possible the at least partial dissolution of said organic additive in the water. This minimum amount of water may not be comparable to a solvent. In this case, and when the step of introduction of the additive is carried out separately from the introduction of the precursor of the active phase of the catalyst (i.e. steps a) and b) are carried out separately), each step of bringing the support into contact with the organic additive is advantageously followed by drying at a temperature of less than 250° C., preferably between 15 and 240° C., more preferentially between 30 and 220° C.

The contacting operation according to step a) is generally carried out at a temperature between 0 and 70° C., preferably between 10 and 60° C. and particularly preferably at ambient temperature.

According to step a), the operation of bringing said porous support and the organic additive into contact can be carried out by any method known to those skilled in the art. Preferably, use may be made of convective mixers, drum mixers or static mixers. Step a) is advantageously carried out for a period of time of between 5 minutes and 5 hours, depending on the type of mixer used, preferably between 10 minutes and 4 hours.

According to the invention, the molar ratio of the organic additive to the nickel is greater than 0.05 mol/mol, preferably between 0.1 and 5 mol/mol, more preferentially between 0.12 and 3 mol/mol and more preferably still between 0.15 and 2.5 mol/mol.

Step b)

According to step b), the alumina support is brought into contact with at least one nickel metal salt, at a temperature below the melting point of the metal salt, for a period of time advantageously between 5 minutes and 5 hours, in order to form a solid mixture, the ratio by weight of said metal salt to the alumina support being between 0.1 and 2.3, preferably between 0.2 and 2.

Preferably, the melting point of said metal salt is between 20° C. and 150° C. Preferably, the metal salt is hydrated. Preferably, the metal salt is nickel nitrate hexahydrate (Ni$(NO_3)_2$.$6H_2O$, $T_{melting}$=56.7° C.).

According to step b), the operation of bringing said porous oxide support and the nickel metal salt into contact can be carried out by any method known to those skilled in the art. Preferably, use may be made of convective mixers, drum mixers or static mixers. Step b) is advantageously carried out for a period of time of between 5 minutes and 5 hours, depending on the type of mixer used, preferably between 10 minutes and 4 hours.

In comparison with the prior art described in document U.S. Pat. No. 5,036,032 and which is based on bringing a support into contact in a bath of molten salts, step b) of the process according to the invention makes possible:

optimized control of the amount of metal deposited on the catalyst; and controlled hazardousness and controlled cost of the preparation process by the minimization of the amounts of metal precursor employed, not exceeding 1 gram of metal precursor per 1 gram of support.

Implementation of Steps a) and b)

According to the invention:

steps a) and b) are carried out successively in this order, or steps a) and b) are carried out simultaneously.

In a preferred embodiment, step a) is carried out before carrying out step b).

Step c)

According to step c), the mixture obtained on conclusion of steps a) and b) is heated with stirring to a temperature between the melting point of the metal salt and 200° C., and advantageously at atmospheric pressure. Preferably, the temperature is between 50 and 100° C.

Advantageously, step c) is carried out for a period of time of between 5 minutes and 12 hours, preferably between 5 minutes and 4 hours.

According to step c), the mechanical homogenization of the mixture can be carried out by any method known to those skilled in the art. Preferably, use may be made of convective mixers, drum mixers or static mixers. More preferentially still, step c) is carried out by means of a drum mixer, the rotational speed of which is between 4 and 70 revolutions/minute, preferably between 10 and 60 revolutions/minute. This is because, if the rotation of the drum is too high, the active phase of the catalyst will not be distributed as a crust at the periphery of the support but will be distributed homogeneously throughout the support, which is not desirable.

Step d) Catalyst Precursor Drying

Step d) of drying the catalyst precursor obtained on conclusion of step c) is carried out at a temperature of less than 250° C., preferably of between 15 and 180° C., more preferentially between 30 and 160° C., more preferentially still between 50 and 150° C. and in an even more preferential way between 70 and 140° C., typically for a period of time of between 10 minutes and 24 hours. Longer periods of time are not ruled out but do not necessarily contribute an improvement. The drying temperature of step d) is generally higher than the heating temperature of step c). Preferably, the drying temperature of step d) is at least 10° C. higher than the heating temperature of step c).

The drying step can be carried out by any technique known to those skilled in the art. It is advantageously carried out under an inert atmosphere or under an oxygen-containing atmosphere or under a mixture of inert gas and oxygen. It is advantageously carried out at atmospheric pressure or at reduced pressure. Preferably, this step is carried out at atmospheric pressure and in the presence of air or nitrogen.

Step e) Heat Treatment of the Dried Catalyst

The dried catalyst precursor undergoes an additional heat treatment step, before the optional reduction step f), at a temperature of between 250 and 1000° C. and preferably between 250 and 750° C., typically for a period of time of between 15 minutes and 10 hours, under an inert atmosphere or under an oxygen-containing atmosphere, in the presence or absence of water. Longer treatment times are not ruled out but do not necessarily contribute an improvement.

The term "heat treatment" is understood to mean the treatment in temperature respectively without the presence or in the presence of water. In the latter case, contact with steam can take place at atmospheric pressure or under autogenous pressure. Several combined cycles without the presence or with the presence of water can be carried out. After this or these treatment(s), the catalyst precursor comprises nickel in oxide form, that is to say in NiO form.

In the case of the presence of water, the water content is preferably between 150 and 900 grams per kilogram of dry air and more preferably still between 250 and 650 grams per kilogram of dry air.

Step f) Reduction by a Reducing Gas (Optional Step)

Prior to the use of the catalyst in the catalytic reactor and the implementation of a hydrogenation process, at least one reducing treatment step f) is advantageously carried out in the presence of a reducing gas after step e), so as to obtain a catalyst comprising nickel at least partially in metallic form.

This treatment makes it possible to activate said catalyst and to form metal particles, in particular of nickel in the zero-valent state. Said reducing treatment can be carried out in situ or ex situ, that is to say after or before the catalyst is charged to the hydrogenation reactor.

The reducing gas is preferably hydrogen. The hydrogen can be used pure or as a mixture (for example a hydrogen/nitrogen or hydrogen/argon or hydrogen/methane mixture). In the case where the hydrogen is used as a mixture, all proportions can be envisaged.

Said reducing treatment is carried out at a temperature of between 120 and 500° C., preferably between 150 and 450° C. When the catalyst is not subjected to passivation or is subjected to a reducing treatment before passivation, the reducing treatment is carried out at a temperature of between 180 and 500° C., preferably between 200 and 450° C., and more preferentially still between 350 and 450° C. When the catalyst has been subjected beforehand to a passivation, the reducing treatment is generally carried out at a temperature of between 120 and 350° C., preferably between 150 and 350° C.

The duration of the reducing treatment is generally between 2 and 40 hours, preferably between 3 and 30 hours. The rise in temperature up to the desired reduction temperature is generally slow, for example set between 0.1 and 10° C./min, preferably between 0.3 and 7° C./min.

The hydrogen flow rate, expressed in l/hour/gram of catalyst, is between 0.01 and 100 l/hour/gram of catalyst, preferably between 0.05 and 10 l/hour/gram of catalyst and more preferably still between 0.1 and 5 l/hour/gram of catalyst.

Step g) Passivation (Optional)

The catalyst prepared according to the process according to the invention can advantageously undergo a step of passivation by a sulfur-containing compound which makes it possible to improve the selectivity of the catalysts and to prevent thermal runaways during the start-up of fresh catalysts. The passivation generally consists in irreversibly poisoning, by the sulfur-containing compound, the most virulent active sites of the nickel which exist on the fresh catalyst and in thus weakening the activity of the catalyst in favor of its selectivity. The passivation step is carried out by the use of methods known to those skilled in the art.

The step of passivation by a sulfur-containing compound is generally carried out at a temperature of between 20 and 350° C., preferably between 40 and 200° C., for from 10 to 240 minutes. The sulfur-containing compound is, for example, chosen from the following compounds: thiophene, thiophane, alkyl monosulfides, such as dimethyl sulfide, diethyl sulfide, dipropyl sulfide and propyl methyl sulfide, or also an organic disulfide of formula HO—$R_1$—S—S—$R_2$—OH, such as dithiodiethanol of formula HO—$C_2H_4$—S—S—$C_2H_4$—OH (often referred to as DEODS). The sulfur content is generally between 0.1% and 2% by weight of said element, relative to the total weight of the catalyst.

Selective Hydrogenation Process

The catalyst obtained according to the process according to the invention can be used in a process for the selective hydrogenation of polyunsaturated compounds containing at least 2 carbon atoms per molecule, such as diolefins and/or acetylenics and/or alkenylaromatics, also known as styrenics, contained in a hydrocarbon feedstock having a final boiling point below or equal to 300° C. The process can be carried out at a temperature of between 0° C. and 300° C., at a pressure of between 0.1 and 10 MPa, at a hydrogen/(polyunsaturated compounds to be hydrogenated) mole ratio of between 0.1 and 10 and at an hourly space velocity of between 0.1 and 200 $h^{-1}$ when the process is carried out in the liquid phase, or at a hydrogen/(polyunsaturated compounds to be hydrogenated) mole ratio of between 0.5 and 1000 and at an hourly space velocity of between 100 and 40 000 h-1 when the process is carried out in the gas phase, in the presence of a catalyst obtained by the preparation process as described above in the description.

Monounsaturated organic compounds, such as, for example, ethylene and propylene, are at the root of the manufacture of polymers, of plastics and of other chemicals having added value. These compounds are obtained from natural gas, from naphtha or from gas oil which have been treated by steam cracking or catalytic cracking processes. These processes are carried out at high temperature and produce, in addition to the desired monounsaturated compounds, polyunsaturated organic compounds, such as acetylene, propadiene and methylacetylene (or propyne), 1,2-butadiene and 1,3-butadiene, vinylacetylene and ethylacetylene, and other polyunsaturated compounds, the boiling point of which corresponds to the C5+ fraction (hydrocarbon compounds having at least 5 carbon atoms), in particular diolefinic or styrene or indene compounds. These polyunsaturated compounds are highly reactive and result in side reactions in the polymerization units. It is thus necessary to remove them before making economic use of these fractions.

Selective hydrogenation is the main treatment developed to specifically remove undesirable polyunsaturated compounds from these hydrocarbon feedstocks. It makes possible the conversion of polyunsaturated compounds to the corresponding alkenes or aromatics while avoiding their complete saturation and thus the formation of the corresponding alkanes or naphthenes. In the case of steam cracking gasolines used as feedstock, the selective hydrogenation also makes it possible to selectively hydrogenate the alkenylaromatics to give aromatics while avoiding the hydrogenation of the aromatic rings.

The hydrocarbon feedstock treated in the selective hydrogenation process has a final boiling point of below or equal to 300° C. and contains at least 2 carbon atoms per molecule and comprises at least one polyunsaturated compound. The term "polyunsaturated compounds" is intended to mean compounds comprising at least one acetylenic function and/or at least one diene function and/or at least one alkenylaromatic function.

More particularly, the feedstock is chosen from the group consisting of a steam cracking C2 fraction, a steam cracking C2-C3 fraction, a steam cracking C3 fraction, a steam cracking C4 fraction, a steam cracking C5 fraction and a steam cracking gasoline, also known as pyrolysis gasoline or C5+ fraction.

The steam cracking C2 fraction, advantageously used for the implementation of the selective hydrogenation process, exhibits, for example, the following composition: between 40% and 95% by weight of ethylene and of the order of 0.1% to 5% by weight of acetylene, the remainder being essentially ethane and methane. In some steam cracking C2 fractions, between 0.1% and 1% by weight of C3 compounds may also be present.

The steam cracking C3 fraction, advantageously used for the implementation of the selective hydrogenation process, exhibits, for example, the following mean composition: of the order of 90% by weight of propylene and of the order of 1% to 8% by weight of propadiene and of methylacetylene, the remainder being essentially propane. In some C3 fractions, between 0.1% and 2% by weight of C2 compounds and of C4 compounds may also be present.

A C2-C3 cut can also be advantageously used for carrying out the selective hydrogenation process. It exhibits, for example, the following composition: of the order of 0.1% to 5% by weight of acetylene, of the order of 0.1% to 3% by weight of propadiene and of methylacetylene, of the order of 30% by weight of ethylene and of the order of 5% by weight of propylene, the remainder being essentially methane, ethane and propane. This feedstock may also contain between 0.1% and 2% by weight of C4 compounds.

The steam cracking C4 fraction, advantageously used for the implementation of the selective hydrogenation process, exhibits, for example, the following mean composition by weight: 1% by weight of butane, 46.5% by weight of butene, 51% by weight of butadiene, 1.3% by weight of vinylacetylene and 0.2% by weight of butyne. In some C4 fractions, between 0.1% and 2% by weight of C3 compounds and of C5 compounds may also be present.

The steam cracking C5 fraction, advantageously used for the implementation of the selective hydrogenation process, exhibits, for example, the following composition: 21% by weight of pentanes, 45% by weight of pentenes and 34% by weight of pentadienes.

The steam cracking gasoline or pyrolysis gasoline, advantageously used for the implementation of the selective hydrogenation process, corresponds to a hydrocarbon fraction, the boiling point of which is generally between 0 and 300° C., preferably between 10 and 250° C. The polyunsaturated hydrocarbons to be hydrogenated present in said steam cracking gasoline are in particular diolefin compounds (butadiene, isoprene, cyclopentadiene, and the like), styrene compounds (styrene, α-methylstyrene, and the like) and indene compounds (indene, and the like). The steam cracking gasoline generally comprises the C5-C12 fraction with traces of C3, C4, C13, C14 and C15 (for example between 0.1% and 3% by weight for each of these fractions). For example, a feedstock formed of pyrolysis gasoline generally has a composition as follows: 5% to 30% by weight of saturated compounds (paraffins and naphthenes), 40% to 80% by weight of aromatic compounds, 5% to 20% by weight of mono-olefins, 5% to 40% by weight of diolefins and 1% to 20% by weight of alkenylaromatic compounds, the combined compounds forming 100%. It also contains from 0 to 1000 ppm by weight of sulfur, preferably from 0 to 500 ppm by weight of sulfur.

Preferably, the polyunsaturated hydrocarbon feedstock treated in accordance with the selective hydrogenation process is a steam cracking C2 fraction or a steam cracking C2-C3 fraction or a steam cracking gasoline.

The selective hydrogenation process is targeted at removing said polyunsaturated hydrocarbons present in said feedstock to be hydrogenated without hydrogenating the mono-unsaturated hydrocarbons. For example, when said feedstock is a C2 fraction, the selective hydrogenation process is targeted at selectively hydrogenating acetylene. When said feedstock is a C3 fraction, the selective hydrogenation process is targeted at selectively hydrogenating propadiene and methylacetylene. In the case of a C4 fraction, the aim is to remove butadiene, vinylacetylene (VAC) and butyne; in the case of a C5 fraction, the aim is to remove the pentadienes. When said feedstock is a steam cracking gasoline, the selective hydrogenation process is targeted at selectively hydrogenating said polyunsaturated hydrocarbons present in said feedstock to be treated so that the diolefin compounds are partially hydrogenated to give mono-olefins and so that the styrene and indene compounds are partially hydrogenated to give corresponding aromatic compounds while avoiding the hydrogenation of the aromatic rings.

The technological implementation of the selective hydrogenation process is, for example, carried out by injection, as upflow or downflow, of the polyunsaturated hydrocarbon feedstock and of the hydrogen into at least one fixed bed reactor. Said reactor can be of isothermal type or of adiabatic type. An adiabatic reactor is preferred. The polyunsaturated hydrocarbon feedstock can advantageously be diluted by one or more reinjection(s) of the effluent, resulting from said reactor where the selective hydrogenation reaction takes place, at various points of the reactor, located between the inlet and the outlet of the reactor, in order to limit the temperature gradient in the reactor. The technological implementation of the selective hydrogenation process can also advantageously be carried out by the implantation of at least said supported catalyst in a reactive distillation column or in reactors-exchangers or in a slurry-type reactor. The stream of hydrogen can be introduced at the same time as the feedstock to be hydrogenated and/or at one or more different points of the reactor.

The selective hydrogenation of the steam cracking C2, C2-C3, C3, C4, C5 and C5+ fractions can be carried out in the gas phase or in the liquid phase, preferably in the liquid phase for the C3, C4, C5 and C5+ fractions and in the gas phase for the C2 and C2-C3 fractions. A liquid-phase reaction makes it possible to lower the energy cost and to increase the cycle period of the catalyst.

Generally, the selective hydrogenation of a hydrocarbon feedstock containing polyunsaturated compounds containing at least 2 carbon atoms per molecule and having a final boiling point below or equal to 300° C. is carried out at a temperature of between 0° C. and 300° C., at a pressure of between 0.1 and 10 MPa, at a hydrogen/(polyunsaturated compounds to be hydrogenated) mole ratio of between 0.1 and 10 and at an hourly space velocity HSV (defined as the ratio of the flow rate by volume of feedstock to the volume of the catalyst) of between 0.1 and 200 $h^{-1}$ for a process carried out in the liquid phase, or at a hydrogen/(polyunsaturated compounds to be hydrogenated) mole ratio of between 0.5 and 1000 and at an hourly space velocity HSV of between 100 and 40 000 $h^{-1}$ for a process carried out in the gas phase.

In one embodiment, when a selective hydrogenation process is carried out wherein the feedstock is a steam cracking gasoline comprising polyunsaturated compounds, the (hydrogen)/(polyunsaturated compounds to be hydrogenated) mole ratio is generally between 0.5 and 10, preferably between 0.7 and 5.0 and more preferably still between 1.0 and 2.0, the temperature is between 0° C. and 200° C., preferably between 20° C. and 200° C. and more preferably still between 30° C. and 180° C., the hourly space velocity (HSV) is generally between 0.5 and 100 $h^{-1}$, preferably between 1 and 50 $h^{-1}$, and the pressure is generally between 0.3 and 8.0 MPa, preferably between 1.0 and 7.0 MPa and more preferably still between 1.5 and 4.0 MPa.

More preferentially, a selective hydrogenation process is carried out wherein the feedstock is a steam cracking gasoline comprising polyunsaturated compounds, the hydrogen/(polyunsaturated compounds to be hydrogenated) mole ratio is between 0.7 and 5.0, the temperature is between 20° C. and 200° C., the hourly space velocity (HSV) is generally between 1 and 50 $h^{-1}$ and the pressure is between 1.0 and 7.0 MPa.

More preferentially still, a selective hydrogenation process is carried out wherein the feedstock is a steam cracking gasoline comprising polyunsaturated compounds, the hydrogen/(polyunsaturated compounds to be hydrogenated) mole ratio is between 1.0 and 2.0, the temperature is between 30° C. and 180° C., the hourly space velocity (HSV) is generally between 1 and 50 $h^{-1}$ and the pressure is between 1.5 and 4.0 MPa.

The hydrogen flow rate is adjusted in order to have available a sufficient amount thereof to theoretically hydrogenate all of the polyunsaturated compounds and to maintain an excess of hydrogen at the reactor outlet.

In another embodiment, when a selective hydrogenation process is carried out wherein the feedstock is a steam cracking C2 fraction and/or a steam cracking C2-C3 fraction comprising polyunsaturated compounds, the (hydrogen)/(polyunsaturated compounds to be hydrogenated) mole ratio is generally between 0.5 and 1000, preferably between 0.7 and 800, the temperature is between 0° C. and 300° C., preferably between 15° C. and 280° C., the hourly space velocity (HSV) is generally between 100 and 40 000 $h^{-1}$, preferably between 500 and 30000 $h^{-1}$, and the pressure is generally between 0.1 and 6.0 MPa, preferably between 0.2 and 5.0 MPa.

The invention will now be illustrated via the examples below which are in no way limiting.

EXAMPLES

For all the catalysts mentioned in the examples mentioned below, the support is an alumina AL-1 exhibiting a specific surface of 80 $m^2/g$, a pore volume of 0.7 ml/g and a median mesopore diameter of 12 nm.

Example 1 (Conforms)

10 g of alumina AL-1 support are brought into contact with 1.18 g of citric acid dissolved in 5.4 g of water. The solid thus obtained is subsequently dried in an oven at 60° C. for 2 hours and then at 120° C. for 12 hours.

Subsequently, the support is brought into contact with 9.47 g of nickel nitrate hexahydrate in a pan at 25° C. which rotates at a speed of 40 to 50 revolutions per minute. The pan is subsequently heated to 62° C. and rotates at a speed of 40 to 50 revolutions per minute for 15 minutes. The molar ratio by weight of the citric acid to the nickel is 0.2.

The nickel content targeted with regard to this step is 15% by weight of Ni, relative to the weight of the final catalyst. The solid thus obtained is subsequently dried in an oven at 120° C. overnight and then calcined under a stream of air of 1 l/h/g of catalyst at 450° C. for 2 hours.

The catalyst A containing 15% by weight of the element nickel, relative to the total weight of the catalyst, is obtained. The characteristics of the catalyst A thus obtained are given in table 1 below.

Example 2 (Conforms)

10 g of alumina AL-1 support are brought into contact with 2.36 g of citric acid dissolved in 10 g of water. The solid thus obtained is subsequently dried in an oven at 60° C. for 2 hours and then at 120° C. for 12 hours. Subsequently, the support is brought into contact with 9.47 g of nickel nitrate hexahydrate in a pan at 25° C. which rotates at a speed of 40 to 50 revolutions per minute. The pan is subsequently heated to 62° C. and rotates at a speed of 40 to 50 revolutions per minute for 15 minutes. The citric acid to Ni molar ratio is 0.4.

The nickel content targeted with regard to this step is 15% by weight of Ni, relative to the weight of the final catalyst. The solid thus obtained is subsequently dried in an oven at 120° C. overnight and then calcined under a stream of air of 1 l/h/g of catalyst at 450° C. for 2 hours.

The catalyst B containing 15% by weight of the element nickel, relative to the total weight of the catalyst, is obtained. The characteristics of the catalyst B thus obtained are given in table 1 below.

Example 3 (Conforms)

10 g of alumina AL-1 support are brought into contact with 0.39 g of citric acid dissolved in 5.4 g of water. The solid thus obtained is subsequently dried in an oven at 60° C. for 2 hours and then at 120° C. for 12 hours.

Subsequently, the support is brought into contact with 3.15 g of nickel nitrate hexahydrate in a pan at 25° C. which rotates at a speed of 40 to 50 revolutions per minute. The pan is subsequently heated to 62° C. and rotates at a speed of 40 to 50 revolutions per minute for 15 minutes. The citric acid to Ni molar ratio is 0.2.

The nickel content targeted with regard to this step is 5% by weight of Ni, relative to the weight of the final catalyst. The solid thus obtained is subsequently dried in an oven at 120° C. overnight and then calcined under a stream of air of 1 l/h/g of catalyst at 450° C. for 2 hours.

The catalyst C containing 5% by weight of the element nickel, relative to the total weight of the catalyst, is obtained. The characteristics of the catalyst C thus obtained are given in table 1 below.

Example 4 (Conforms)

10 g of AL-1 alumina support are brought into contact with 0.47 g of glycolic acid dissolved in 5.4 g of water. The solid thus obtained is subsequently dried in an oven at 60° C. for 2 hours and then at 120° C. for 12 hours.

Subsequently, the support is brought into contact with 9.47 g of nickel nitrate hexahydrate in a pan at 25° C. which rotates at a speed of 40 to 50 revolutions per minute. The pan is subsequently heated to 62° C. and rotates at a speed of 40 to 50 revolutions per minute for 15 minutes. The glycolic acid to Ni molar ratio is 0.2.

The Ni content targeted with regard to this step is 15% by weight of Ni, relative to the weight of the final catalyst. The solid thus obtained is subsequently dried in an oven at 120° C. overnight and then calcined under a stream of air of 1 l/h/g of catalyst at 450° C. for 2 hours.

The catalyst D containing 15% by weight of the element nickel, relative to the total weight of the catalyst, is obtained. The characteristics of the catalyst D thus obtained are given in table 1 below.

Example 5 (Not in Accordance)

10 g of alumina AL-1 support are dry impregnated with 9.47 g of nickel nitrate hexahydrate in a pan at 25° C. which rotates at a speed of 40 to 50 revolutions per minute. The pan is subsequently heated to 62° C. and rotates at a speed of 40 to 50 revolutions per minute for 15 minutes.

The Ni content targeted with regard to this step is 15% by weight of Ni, relative to the weight of the final catalyst. The solid thus obtained is subsequently dried in an oven at 120° C. overnight and then calcined under a stream of air of 1 l/h/g of catalyst at 450° C. for 2 hours.

The catalyst E containing 15% by weight of the element nickel, relative to the total weight of the catalyst, is obtained. The characteristics of the catalyst E thus obtained are given in table 1 below.

Example 6: Characterization

All the catalysts contain the contents targeted during the impregnation, that is to say 15% for examples 1, 2, 4 and 5 and 5% for example 3 of nickel element (characterized by X-ray fluorescence), relative to the total weight of the catalyst.

The sizes of NiO particles obtained after the calcination step was determined by X-ray diffraction (XRD) analysis on samples of catalyst in powder form.

| Catalyst | Ni content (wt %) | Particle size (nm) |
|---|---|---|
| A (in accordance) | 15 | 2 |
| B (in accordance) | 15 | 2.5 |
| C (in accordance) | 5 | 2 |
| D (in accordance) | 15 | 2 |
| E (not in accordance) | 15 | 20 |

Example 7: Catalytic Tests: Performance Levels in Selective Hydrogenation of a Mixture Containing Styrene and Isoprene ($A_{HYD1}$)

Catalysts A to E described in the examples above are tested with regard to the reaction for the selective hydrogenation of a mixture containing styrene and isoprene.

The composition of the feedstock to be selectively hydrogenated is as follows: 8% by weight of styrene (supplied by Sigma Aldrich®, purity 99%), 8% by weight of isoprene (supplied by Sigma Aldrich®, purity 99%) and 84% by weight of n-heptane (solvent) (supplied by VWR®, purity>99% Chromanorm HPLC). This feedstock also contains sulfur-containing compounds in a very small content: 10 ppm by weight of sulfur introduced in the form of pentanethiol (supplied by Fluka®, purity>97%) and 100 ppm by weight of sulfur introduced in the form of thiophene (supplied by Merck®, purity 99%). This composition corresponds to the initial composition of the reaction mixture. This mixture of model molecules is representative of a pyrolysis gasoline.

The selective hydrogenation reaction is carried out in a 500 ml stainless steel autoclave which is provided with a magnetically-driven mechanical stirrer and which is able to operate under a maximum pressure of 100 bar (10 MPa) and temperatures of between 5° C. and 200° C.

Prior to its introduction into the autoclave, an amount of 3 ml of catalyst is reduced ex situ under a stream of hydrogen of 1 l/h/g of catalyst at 400° C. for 16 hours (temperature rise gradient of 1° C./min) and then it is transferred into the autoclave, with the exclusion of air. After addition of 214 ml of n-heptane (supplied by VWR®, purity>99% Chromanorm HPLC), the autoclave is closed, purged, then pressurized under 35 bar (3.5 MPa) of hydrogen and brought to the temperature of the test, which is equal to 30° C. At the time t=0, approximately 30 g of a mixture containing styrene, isoprene, n-heptane, pentanethiol and thiophene are introduced into the autoclave. The reaction mixture then has the composition described above and stirring is started at 1600 rpm. The pressure is kept constant at 35 bar (3.5 MPa) in the autoclave using a storage cylinder located upstream of the reactor.

The progress of the reaction is monitored by taking samples from the reaction medium at regular time intervals: the styrene is hydrogenated to give ethylbenzene, without hydrogenation of the aromatic ring, and the isoprene is hydrogenated to give methylbutenes. If the reaction is prolonged for longer than necessary, the methylbutenes are in their turn hydrogenated to give isopentane. The hydrogen consumption is also monitored over time by the decrease in pressure in a storage cylinder located upstream of the reactor. The catalytic activity is expressed in moles of $H_2$ consumed per minute and per gram of Ni.

The catalytic activities measured for catalysts A to E are reported in table 2 below. They are related back to the catalytic activity ($A_{HYD1}$) measured for catalyst C.

| Catalyst | Ni content (%) | Size of the Ni° particles (nm) | $A_{HYD}$ (%) |
| --- | --- | --- | --- |
| A (in accordance) | 15 | 2 | 300 |
| B (in accordance) | 15 | 2.5 | 280 |
| C (in accordance) | 5 | 2 | 100 |
| D (in accordance) | 15 | 2 | 300 |
| E (not in accordance) | 15 | 20 | 50 |

The catalysts A, B and D according to the invention result in very high selective hydrogenation activities. Furthermore, the preparation process according to the invention in example 3, catalyst C, makes it possible to add only 5% by weight of nickel to the support while obtaining a correct selective hydrogenation activity. In example 5, the additive was not added, which results in the catalyst E with a greatly reduced activity due to the size of the nickel particles of 20 nm, i.e. 10 times greater than for the catalysts according to the invention.

The invention claimed is:

1. A selective hydrogenation catalyst comprising a nickel-based active phase and an alumina support, said active phase not comprising a metal from Group VIB, said catalyst comprising a content of elemental nickel of greater than or equal to 1% by weight and less than 20% by weight relative to the total weight of the catalyst in a form of particles, the size of the nickel particles in the catalyst, measured in oxide form, is less than 18 nm, said catalyst being capable of being obtained by a process comprising at least the following steps:
   a) the alumina support is brought into contact with at least one organic additive in the form of a powder dissolved in a minimum amount of water, the organic additive comprising oxygen and/or nitrogen, the molar ratio of the organic additive to the nickel being greater than 0.05 mol/mol;
   b) the alumina support is brought into contact with at least one nickel metal salt, at a temperature of less than the melting point of said nickel metal salt, in order to form a solid mixture, the ratio by weight of said metal salt to the alumina support being between 0.1 and 2.3,
      steps a) and b) being carried out either successively in this order, or simultaneously;
   c) the solid mixture obtained on conclusion of steps a) and b) is heated with stirring to a temperature between the melting point of said metal salt and 200° C., in order to obtain a catalyst precursor;
   d) the catalyst precursor on conclusion of step c) is dried at a temperature of less than 250° C. in order to obtain a dried catalyst precursor;
   e) a step of heat treatment of the dried catalyst precursor obtained on conclusion of step d) is carried out at a temperature of between 250 and 1000° C.

2. The catalyst as claimed in claim 1, wherein the size of the nickel particles in the catalyst, measured in oxide form, is between 0.5 and 12 nm.

3. The catalyst as claimed in claim 1, wherein the size of the nickel particles in the catalyst, measured in oxide form, is between 1 and 5 nm.

4. The catalyst as claimed in claim 1, wherein the size of the nickel particles in the catalyst, measured in oxide form, is between 2 and 2.5 nm.

5. A process for preparing a selective hydrogenation catalyst comprising a nickel-based active phase and an alumina support, said active phase not comprising a metal from Group VIB, said catalyst comprising a content of elemental nickel of greater than or equal to 1% by weight and less than 20% by weight relative to the total weight of the catalyst in a form of particles, the nickel particle size in the catalyst, measured in oxide form, is less than 18 nm, said process comprising the following steps:
   a) the alumina support is brought into contact with at least one organic additive in the form of a powder dissolved in a minimum amount of water, the organic additive comprising oxygen and/or nitrogen, the molar ratio of the organic additive to the nickel being greater than 0.05 mol/mol;
   b) the alumina support is brought into contact with at least one nickel metal salt, at a temperature of less than the melting point of said nickel metal salt, in order to form a solid mixture, the ratio by weight of said metal salt and the alumina support being between 0.1 and 2.3, steps a) and b) being carried out successively in this order, or simultaneously;
   c) the solid mixture obtained on conclusion of stages a) and b) is heated with stirring to a temperature between the melting point of said metal salt and 200° C., in order to obtain a catalyst precursor;
   d) the catalyst precursor on conclusion of step c) is dried at a temperature of less than 250° C. in order to obtain a dried catalyst precursor;
   e) a step of heat treatment of the dried catalyst precursor obtained on conclusion of step d) is carried out at a temperature of between 250 and 1000° C.

6. The process as claimed in claim 5, wherein the melting point of said metal salt is between 20° C. and 150° C.

7. The process as claimed in claim 5, wherein the molar ratio of said organic additive introduced in step a) to the element nickel introduced in step b) is between 0.1 and 5.0 mol/mol.

8. The process as claimed in claim 5, wherein steps a) and b) are carried out simultaneously.

9. The process as claimed in claim 5, wherein said organic additive of step a) is chosen from formic acid, formaldehyde, acetic acid, citric acid, oxalic acid, glycolic acid, malonic acid, levulinic acid, ethanol, methanol, ethyl formate, methyl formate, paraldehyde, acetaldehyde, γ-valerolactone, glucose and sorbitol.

10. The process as claimed in claim 5, wherein the organic additive of step a) is chosen from citric acid, formic acid, glycolic acid, levulinic acid and oxalic acid.

11. The process as claimed in claim 5, wherein step c) is carried out by a pan operating at a speed of between 4 and 70 revolutions per minute.

12. The process as claimed in claim 5, wherein, in step b), the ratio by weight of said metal salt to the alumina support is between 0.2 and 2.

13. A process for the selective hydrogenation of polyunsaturated compounds containing at least 2 carbon atoms per molecule, contained in a hydrocarbon feedstock having a final boiling point below or equal to 300° C., which process being carried out at a temperature of between 0° C. and 300° C., at a pressure of between 0.1 and 10 MPa, at a hydrogen/(polyunsaturated compounds to be hydrogenated) mole ratio of between 0.1 and 10 and at an hourly space velocity of between 0.1 and 200 $h^{-1}$ when the process is carried out in a liquid phase, or at a hydrogen/(polyunsaturated compounds to be hydrogenated) mole ratio of between 0.5 and 1000 and at an hourly space velocity of between 100 and 40 000 $h^{-1}$ when the process is carried out in a gas phase, in the presence of a catalyst as claimed in claim 1.

14. A process for the selective hydrogenation of polyunsaturated compounds containing at least 2 carbon atoms per molecule, contained in a hydrocarbon feedstock having a final boiling point below or equal to 300° C., which process being carried out at a temperature of between 0° C. and 300° C., at a pressure of between 0.1 and 10 MPa, at a hydrogen/(polyunsaturated compounds to be hydrogenated) mole ratio of between 0.1 and 10 and at an hourly space velocity of between 0.1 and 200 h$^{-1}$ when the process is carried out in a liquid phase, or at a hydrogen/(polyunsaturated compounds to be hydrogenated) mole ratio of between 0.5 and 1000 and at an hourly space velocity of between 100 and 40 000 h$^{-1}$ when the process is carried out in a gas phase, in the presence of a catalyst obtained by the process as claimed in claim 5.

15. A selective hydrogenation catalyst comprising a nickel-based active phase and an alumina support, said active phase not comprising a metal from Group VIB, said catalyst comprising a content of elemental nickel of greater than or equal to 1% by weight and less than 20% by weight relative to the total weight of the catalyst in a form of particles, the size of the nickel particles in the catalyst, measured in oxide form, being 1 to 5 nm, said catalyst being capable of being obtained by a process comprising at least the following steps:
  a) the alumina support is brought into contact with at least one organic additive in the form of a powder dissolved in a minimum amount of water, the organic additive comprising citric acid, formic acid, glycolic acid, levulinic acid or oxalic acid, the molar ratio of the organic additive to the nickel being greater than 0.05 mol/mol;
  b) the alumina support is brought into contact with at least one nickel metal salt, at a temperature of less than the melting point of said nickel metal salt, in order to form a solid mixture, the ratio by weight of said metal salt to the alumina support being between 0.1 and 2.3,
    steps a) and b) being carried out either successively in this order, or simultaneously;
  c) the solid mixture obtained on conclusion of steps a) and b) is heated with stirring to a temperature between the melting point of said metal salt and 200° C., in order to obtain a catalyst precursor;
  d) the catalyst precursor on conclusion of step c) is dried at a temperature of less than 250° C. in order to obtain a dried catalyst precursor;
  e) a step of heat treatment of the dried catalyst precursor obtained on conclusion of step d) is carried out at a temperature of between 250 and 1000° C.

* * * * *